United States Patent [19]

Berg et al.

[11] Patent Number: 4,732,653

[45] Date of Patent: * Mar. 22, 1988

[54] SEPARATION OF ETHANOL FROM T-BUTANOL BY EXTRACTIVE DISTILLATION

[76] Inventors: Lloyd Berg; Mark G. Vosburgh, both of 1314 S. Third Ave., Bozeman, Mont. 59715

[*] Notice: The portion of the term of this patent subsequent to Dec. 1, 2004 has been disclaimed.

[21] Appl. No.: 784,870

[22] Filed: Oct. 7, 1985

[51] Int. Cl.$^4$ .................. B01D 3/40; C07C 29/84
[52] U.S. Cl. ................................ 203/51; 203/60; 203/61; 568/913
[58] Field of Search ............... 203/51, 60, 61, 64, 203/56; 568/918, 913

[56] References Cited

U.S. PATENT DOCUMENTS

| | | | |
|---|---|---|---|
| 2,551,584 | 5/1951 | Carlson et al. | 203/51 |
| 2,552,412 | 5/1951 | Drout et al. | 203/84 |
| 2,559,519 | 7/1951 | Smith et al. | 203/64 |
| 2,559,520 | 7/1951 | Smith et al. | 203/64 |
| 2,570,205 | 10/1951 | Carlson et al. | 203/58 |
| 2,575,243 | 11/1951 | Carlson et al. | 203/60 |
| 2,591,712 | 4/1952 | Morrell et al. | 203/84 |
| 2,591,713 | 4/1952 | Morrell et al. | 203/84 |
| 2,706,707 | 4/1955 | Morrell et al. | 203/57 |

*Primary Examiner*—Wilbur Bascomb

[57] ABSTRACT

Ethanol and t-butanol cannot be separated from each other by distillation because of the proximity of their boiling points. Ethanol can be readily separated from t-butanol by using extractive distillation in which the extractive agent is a higher boiling oxygenated organic compound or a mixture of two or more of these. Typical examples of effective agents are: methyl benzoate; benzyl benzoate and benzoic acid; methyl salicylate, hexahydrophthalic anhydride and salicylic acid.

11 Claims, No Drawings

SEPARATION OF ETHANOL FROM T-BUTANOL BY EXTRACTIVE DISTILLATION

FIELD OF THE INVENTION

This invention relates to a method for separating ethanol from tertiary butanol using certain higher boiling liquids as the extractive agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Centigrade degrees or more higher than the lowest boiling component.

At the bottom of a continuous column, the less volatile components of the close boiling mixture and the extractive agent are continuously removed from the column. The usual methods of separation of these two components are the use of another rectification column, cooling and phase separation, or solvent extraction.

Ethanol and t-butanol are two widely used alcohols in commerce today. When they are used as solvents, they frequently end up as a mixture of solvents. Whenever practical, it is mandatory to recover the solvent and re-use it.

Ethanol and t-butanol are both manufactured by the hydration of the corresponding olefin, ethylene for ethanol and isobutylene for t-butanol. At present the ethylene and isobutylene are separated to high purity before reaction with sulfuric acid and water to make the alcohol to avoid the formation of a mixture of these two alcohols in the reaction product. The usual way of recovering liquid components is by distillation in a multiplate rectification column. Ethanol boils at 78.4° C., t-butanol boils at 82.6° C. which gives a relative volatility of ethanol to t-butanol of 1.11, making it virtually impossible to separate these two by conventional rectification.

Extractive distillation would be an attractive method of effecting the separation of ethanol from t-butanol if agents can be found that (1) will alter the relative volatility between ethanol and t-butanol, (2) form no azeotrope with ethanol or t-butanol and (3) are easy to recover from t-butanol, that is boil sufficiently above t-butanol to make separation by rectification possible with only a few theoretical plates.

Extractive distillation typically requires the addition of an equal amount to twice as much extractive agent as the ethanol- t-butanol on each plate of the rectication column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification is another column. In order to keep the cost of this operation to a minimum, an appreciable boiling point difference between the compound being separated and the extractive agent is desirable. It is also desirable that the extractive agent be miscible with the t-butanol otherwise it will form a two phase azeotrope with it and some other method of separation will have to be employed.

C. S. Carlson & P. V. Smith, U.S. Pat. No. 2,570,205 described an extractive distillation process to separate ethanol from isopropanol using sulfolane as the agent. Smith, U.S. Pat. No. 2,559,519 described an extractive distillation process to separate n-propanol from 2-butanol using ethylene glycol butyl ether and diethylene glycol ethyl ether as extractive agents. Smith, U.S. Pat. No. 2,559,520 reported 1,3-butanediol as the extractive agent for the same separation.

OBJECTIVE OF THE INVENTION

The object of this invention is to provide a process or methaod of extractive distillation that will enhance the relative volatility of ethanol from t-butanol in their separation in a rectification column. It is a further objective of this invention to identify organic compounds which are stable, can be separated from t-butanol by rectification with relatively few plates and can be recycled to the extractive distillation column and re-used with little decomposition.

SUMMARY OF THE INVENTION

The objects of this invention are provided by a process for separating ethanol from t-butanol which entails the use of certain oxygenated organic compounds as the agent in extractive distillation.

DETAILED DESCRIPTION OF THE INVENTION

We have discovered that certain oxygenated organic compounds, some individually but principally as mixtures, will effectively enhance the relative volatility between ethanol and t-butanol and permit the separation of pure ethanol from t-butanol by rectification when employed as the agent in extractive distillation. Table 1 lists benzoates, their mixtures and approximate proportions that we have found to be effective. Table 2 is a similar listing for phthalic anhydride and some of its derivatives that also are effective. The data in Tables 1 and 2 were obtained in a vapor-liquid equilibrium still. In each case the starting material was the 50 - 50% ethanol - t-butanol mixture. The ratios are the parts of extractive agent used per part of ethanol - t-butanol mixture. The relative volatilities are listed for each of the two ratios employed.

The compounds that are effective as extractive distillation agents when used alone are methyl benzoate, benzyl benzoate and methyl salicylate. The compounds which are effective when used in mixtures of two or more components are benzoic acid, cinnamic acid, dipropylene glycol dibenzoate, salicylic acid, phthalic anhydride, hexahydrophthalic anhydride, methyl hexahydrophthalic anhydride, methyl tetrahydrophthalic anhydride & trimellitic anhydride. The ratios in Tables 1 and 2 are the parts of extractive agent used per part of ethanol - t-butanol mixture. The two relative volatilities correspond to the two different ratios. For example in Table 1, one part of methyl benzoate with one part of ethanol - t-butanol mixture gives a relative volatility 1.28, 6/5 parts of methyl benzoate gives 1.23. One half part of methyl benzoate mixed with one half part of cinnamic acid with one part of ethanol - t-butanol mixture gives a relative volatility of 1.27, 3/5 parts of methyl benzoate plus 3/5 parts of cinnamic acid gives 1.50. One third parts of methyl salicylate plus ⅓ parts of cinnamic acid plus ⅓ parts of benzoic acid mixed with one part of ethanol - t-butanol mixture gives a relative volatilty of 1.25, with 2/5 parts, these three give 1.34.

In every example in Table 1 and 2 the starting material is a 50-50% mixture of ethanol - t-butanol which possesses a relative volatility of 1.11.

Three of the compounds listed in Table 1 and whose relative volatility had been determined in the vapor-liquid equilibrium still, were then evaluated in a glass perforated plate rectification column possessing 4.5 theoretical plates. The results are listed in Table 3. The ethanol - t-butanol mixture used contained about 75% ethanol. The first run is with methyl benzoate as the extractive agent and a relative volatility of 1.26 was obtained. This compares with the 1.26 and 1.23 shown for methyl benzoate in Table 1, the data for which was obtained in the vapor-liquid equilibrium still.

TABLE 1

Extractive Agents Which Contain Benzoates

| Compounds | Ratios | | Relative Volatilities | |
|---|---|---|---|---|
| None | — | | 1.11 | |
| Methyl benzoate | 1 | 6/5 | 1.28 | 1.23 |
| Methyl benzoate, Benzoic acid | $(1/2)^2$ | $(3/5)^2$ | 1.25 | 1.27 |
| Methyl benzoate, Cinnamic acid | $(1/2)^2$ | $(3/5)^2$ | 1.27 | 1.50 |
| Methyl benzoate, Dipropylene glycol dibenzoate(DPGB) | $(1/2)^2$ | $(3/5)^2$ | 1.20 | 1.24 |
| Methyl benzoate, Hexahydrophthalic anhydride(HHPA) | $(1/2)^2$ | $(3/5)^2$ | 1.26 | 1.26 |
| Methyl benzoate, Salicylic acid | $(1/2)^2$ | $(3/5)^2$ | 1.28 | 1.29 |
| Methyl benzoate, Trimellitic anhydride | $(1/2)^2$ | $(3/5)^2$ | 1.33 | 1.26 |
| Methyl benzoate, Benzoic acid, HHPA | $(1/3)^3$ | $(2/5)^3$ | 1.35 | 1.47 |
| Methyl benzoate, Benzoic acid, Phthalic anhydride | $(1/3)^3$ | $(2/5)^3$ | 1.36 | 1.40 |
| Methyl benzoate, Benzoic acid, Salicylic acid | $(1/2)^3$ | $(2/5)^3$ | 1.23 | 1.27 |
| Methyl benzoate, DPGB, Phthalic anhydride | $(1/3)^3$ | $(2/5)^3$ | 1.20 | 1.17 |
| Methyl benzoate, DPGB, HHPA | $(1/3)^3$ | $(2/5)^3$ | 1.31 | 1.24 |
| Methyl benzoate, HHPA, Cinnamic acid | $(1/3)^3$ | $(2/5)^3$ | 1.38 | 1.44 |
| Methyl benzoate, HHPA, Phthalic anhydride | $(1/3)^3$ | $(2/5)^3$ | 1.36 | 1.52 |
| Methyl benzoate, HHPA, Salicylic acid | $(1/3)^3$ | $(2/5)^3$ | 1.28 | 1.29 |
| Methyl benzoate, Methyl tetrahydrophthalic anh., DPGB | $(1/3)^3$ | $(2/5)^3$ | 1.26 | 1.23 |
| Methyl benzoate, Methyl tetrahydrophthalic anh., Salicylic acid | $(1/3)^3$ | $(2/5)^3$ | 1.30 | 1.40 |
| Methyl benzoate, Methyl HHPA, Benzoic acid | $(1/3)^3$ | $(2/5)^3$ | 1.31 | 1.30 |
| Methyl benzoate, Methyl HHPA, DPGB | $(1/3)^3$ | $(2/5)^3$ | 1.20 | 1.24 |
| Methyl benzoate, Methyl HHPA, Cinnamic acid | $(1/3)^3$ | $(2/5)^3$ | 1.33 | 1.33 |
| Methyl benzoate, Methyl HHPA, Phthalic anhydride | $(1/3)^3$ | $(2/5)^3$ | 1.51 | 1.81 |
| Methyl benzoate, Salicylic acid, Trimellitic anhydride | $(1/3)^3$ | $(2/5)^3$ | 1.49 | 1.22 |
| Benzyl benzoate | 1 | 6/5 | 1.18 | 1.19 |
| Benzyl benzoate, Benzoic acid | $(1/2)^2$ | $(3/5)^2$ | 1.23 | 1.27 |
| Benzyl benzoate, HHPA | $(1/2)^2$ | $(3/5)^2$ | 1.28 | 1.27 |
| Benzyl benzoate, Methyl HHPA | $(1/2)^2$ | $(3/5)^2$ | 1.25 | 1.24 |
| Benzyl benzoate, HHPA, Benzoic acid | $(1/3)^3$ | $(2/5)^3$ | 1.46 | 1.45 |
| Benzyl benzoate, HHPA, Phthalic anhydrid | $(1/3)^3$ | $(2/5)^3$ | 1.71 | 1.76 |
| Benzyl benzoate, HHPA, Salicylic acid | $(1/3)^3$ | $(2/5)^3$ | 1.41 | 1.44 |
| Benzyl benzoate, Methyl HHPA, Phthalic anhydride | $(1/3)^3$ | $(2/5)^3$ | 1.36 | 1.43 |
| o-Hydroxy methyl benzoate (Methyl salicylate) | 1 | 6/5 | 1.22 | 1.28 |
| Methyl salicylate, Benzoic acid | $(1/2)^2$ | $(3/5)^2$ | 1.30 | 1.24 |
| Methyl salicylate, Cinnamic acid | $(1/2)^2$ | $(3/5)^2$ | 1.30 | 1.30 |
| Methyl salicylate, DPGB | $(1/2)^2$ | $(3/5)^2$ | 1.24 | 1.24 |
| Methyl salicylate, HHPA | $(1/2)^2$ | $(3/5)^2$ | 1.44 | 1.34 |
| Methyl salicylate, Methyl HHPA | $(1/2)^2$ | $(3/5)^2$ | 1.30 | 1.24 |
| Methyl salicylate, Benzoic acid, Cinnamic acid | $(1/3)^3$ | $(2/5)^3$ | 1.25 | 1.34 |
| Methyl salicylate, Benzoic acid, HHPA | $(1/3)^3$ | $(2/5)^3$ | 1.22 | 1.31 |
| Methyl salicylate, Benzoic acid, Methyl HHPA | $(1/3)^3$ | $(2/5)^3$ | 1.33 | 1.21 |
| Methyl salicylate, HHPA, DPGB | $(1/3)^3$ | $(2/5)^3$ | 1.29 | 1.24 |
| Methyl salicylate, HHPA, Salicylic acid | $(1/3)^3$ | $(2/5)^3$ | 1.42 | 1.64 |
| Methyl salicylate, Salicylic acid, Trimellitic anhyd. | $(1/3)^3$ | $(2/5)^3$ | 1.33 | 1.38 |

TABLE 2

Extractive Agents Which Contain Derivatives of Phthalic Anhydride

| Compounds | Ratios | | Relative Volatilities | |
|---|---|---|---|---|
| Hexahydrophthalic anhydride (HHPA), Benzoic acid | $(1/2)^2$ | $(3/5)^2$ | 1.32 | 1.55 |
| HHPA, Cinnamic acid | $(1/2)^2$ | $(3/5)^2$ | 1.77 | 1.45 |
| HHPA, Dipropylene glycol dibenzoate (DPGB) | $(1/2)^2$ | $(3/5)^2$ | 1.29 | 1.26 |
| HHPA, Methyl Hexahydrophthalic anhydride (MeHHPA) | $(1/2)^2$ | $(3/5)^2$ | 1.49 | 1.51 |
| HHPA, Phthalic anhydride | $(1/2)^2$ | $(3/5)^2$ | 2.03 | 1.83 |
| HHPA, Salicylic acid | $(1/2)^2$ | $(3/5)^2$ | 1.43 | 1.48 |
| HHPA, MeHHPA, Phthalic anhydride | $(1/3)^3$ | $(2/5)^3$ | 1.60 | 1.36 |
| Methyl tetrahydrophtalic anhydride (MeTHPA), DPGB | $(1/2)^2$ | $(3/5)^2$ | 1.62 | 1.42 |

TABLE 2-continued

Extractive Agents Which Contain Derivatives of Phthalic Anhydride

| Compounds | Ratios | | Relative Volatilities | |
|---|---|---|---|---|
| MeTHPA, Salicylic acid | $(1/2)^2$ | $(3/5)^2$ | 1.31 | 1.36 |
| Methyl hexahydrophthalic anhyd. (MeHHPA), Benzoic acid | $(1/2)^2$ | $(3/5)^2$ | 1.22 | 1.40 |
| MeHHPA, DPGB | $(1/2)^2$ | $(3/5)^2$ | 1.31 | 1.47 |
| MeHHPA, Phthalic anhydride | $(1/2)^2$ | $(3/5)^2$ | 2.03 | 1.89 |
| MeHHPA, Salicylic acid | $(1/2)^2$ | $(3/5)^2$ | 1.36 | 1.55 |

TABLE 3

Data From Runs Made In Rectification Column.

| Agent | Time min. | Stillpot Temp. °C. At Start | Stillpot Temp. °C. Sampling | Overhead Temp. When Sampling | Weight % Ethanol Overhead | Weight % Ethanol Bottoms | Relative Volatility |
|---|---|---|---|---|---|---|---|
| Methyl benzoate | 60 | 80.0 | 90.2 | 76.4 | 82.4 | 64.5 | 1.23 |
| Methyl benzoate | 90 | 80.0 | 95.4 | 76.2 | 83.0 | 63.9 | 1.25 |
| Methyl benzoate | 120 | 80.0 | 100.2 | 76.4 | 84.8 | 62.8 | 1.30 |
| | | | | | | Average = | 1.26 |
| Methyl benzoate, Salicylic acid | 60 | 78.8 | 100.4 | 76.2 | 85.4 | 63.0 | 1.32 |
| Methyl benzoate Salicylic acid | 90 | 78.8 | 107.8 | 76.0 | 86.8 | 62.7 | 1.36 |
| Methyl benzoate Salicylic acid | 120 | 78.8 | 114.4 | 76.2 | 85.7 | 63.2 | 1.34 |
| | | | | | | Average = | 1.34 |
| Methyl salicylate | 60 | 79.2 | 89.2 | 75.2 | 80.8 | 60.3 | 1.25 |
| Methyl salicylate | 90 | 79.2 | 91.4 | 75.2 | 80.9 | 59.1 | 1.25 |
| Methyl salicylate | 120 | 79.2 | 96.2 | 75.2 | 82.4 | 59.1 | 1.30 |
| | | | | | | Average = | 1.27 |

Notes for Table 3

| Agent | Feed, Wt. % EtOH | Agent Rate of Flow, ml/min | Boilup Rate ml/min. | Agent Temp. °C. | Composition of Agent, Wt. % |
|---|---|---|---|---|---|
| Methyl benzoate | 50 | 20 | 10–20 | 70–75 | 100% MeBn |
| Methyl benzoate, Salicylic acid | 50 | 20 | 10–20 | 70–75 | 80% MeBn |
| Methyl salicylate | 50 | 20 | 10–20 | 70–75 | 100% MeSal |

The second run is with a mixture comprising 80% methyl benzoate, 20% salicylic acid. This agent gives a relative volatility of 1.34 which compares with 1.26 and 1.25 shown in Table 1. The third run is with methyl salicylate which gave an average relative volatility of 1.27 after two hours of steady operation. This can be compared with 1.22 and 1.28 shown in Table 1.

THE USEFULNESS OF THE INVENTION

The usefulness or utility of this invention can be demonstrated by referring to the data presented in Table 1, 2 and 3. All of the successful extractive distillation agents show that ethanol can be removed from t-butanol by means of distillation in a rectification column and that the ease of separation as measured by relative volatility is considerable. Without these extractive distillation agents, virtually no improvement will occur in the rectification column. The data also show that the most attractive agents will operate at a boilup rate low enough to make this a useful and efficient method of recovering high purity ethanol from any mixture with t-butanol. The stability of the compounds used and the boiling point difference is such that complete recovery and recycle is obtainable by a simple distillation and the amount required for make-up is small.

WORKING EXAMPLES

EXAMPLE 1

Twenty-five grams of ethanol, 25 grams of t-butanol and fifty grams of methyl benzoate were charged to an Othmer type glass vapor-liquid equilibrium still and refluxed for five hours. Analysis of the vapor and liquid by gas chromatography gave a vapor composition of 69% ethanol, 31% t-butanol; a liquid composition of 63.5% ethanol, 36.5% t-butanol. This indicates a relative volatility of 1.28. Ten grams of methyl benzoate were added and refluxing continued for another six hours. Analysis indicated a vapor composition of 68.2% ethanol, 31.8% t-butanol; a liquid composition of 63.5% ethanol, 36.5% t-butanol which is a relative volatility of 1.23.

EXAMPLE 2

Fifty grams of the ethanol - t-butanol mixture, 25 grams of methyl benzoate and 25 grams of salicylic acid were charged to the vapor-liquid equilibrium still and refluxed for eleven hours. Analysis indicated a vapor composition of 68.5% ethanol, 31.5% t-butanol; a liquid composition of 63% ethanol, 37% t-butanol which is a relative volatility of 1.29. Five grams of methyl benzoate and five grams of salicylic acid were added and refluxing continued for another seven hours. Analysis indicated a vapor composition of 68.6% ethanol, 31.4% t-butanol; a liquid composition of 62.8% ethanol, 37.2% t-butanol which is a relative volatility of 1.29.

EXAMPLE 3

Fifty grams of the ethanol - t-butanol mixture, 17 grams of methyl salicylate, 17 grams of cinnamic acid and 17 grams of benzoic acid were charged to the vapor-liquid equilibrium still and refluxed for thirteen hours. Analysis indicated a vapor composition 69.1% ethanol, 30.9% t-butanol; a liquid composition of 64.2% ethanol, 35.8% t-butanol which is a relative volatility of 1.25. Three grams each of methyl salicylate, cinnamic acid and benzoic acid were added and refluxing continued for another ten hours. Analysis indicated a vapor composition of 68.5% ethanol, 31.5% t-butanol; a liquid composition of 61.8% ethanol, 38.2% t-butanol which is a relative volatility of 1.34.

EXAMPLE 4

A glass perforated plate rectification column was calibrated with ethylbenzene and p-xylene which possesses a relative volatility of 1.06 and found to have 4.5 theoretical plates. A solution of 300 grams of ethanol and 100 grams of t-butanol was placed in the stillpot and heated. When refluxing began, an extractive agent consisting of pure methyl benzoate was pumped into the column at a rate of 20 ml/min. The temperature of the extractive agent as it entered the column was 70°–75° C. After establishing the feed rate of the extractive agent, the heat input to the ethanol - t-butanol in the stillpot was adjusted to give a reflux rate of 10–20 ml/min. After one hour of operation, overhead and bottoms samples of approximately two ml. were collected and analysed using gas chromatography. The overhead analysis was 82.4% ethanol, 17.6% t-butanol. The bottoms analysis was 64.5% ethanol, 35.5% t-butanol. Using these compositions in the Fenske equation, with the number of theoretical plates in the column being 4.5, gave an average relative volatility of 1.23 for each theoretical plate. After 1.5 hours of total operating time, the overhead and bottoms samples were again taken and analysed. The overhead composition was 83% ethanol, 17% t-butanol and the bottoms composition was 63.9% ethanol, 36.1% t-butanol. This gave an average relative volatility of 1.25 for each theoretical plate. After two hours of total operating time, the overhead and bottoms samples were again taken and analysed. The overhead composition was 84.8% ethanol, 15.2% t-butanol and the bottoms composition was 62.8% ethanol, 37.2% t-butanol. This gave an average relative volatility of 1.30 for each theoretical plate.

EXAMPLE 5

A solution of 300 grams of ethanol and 100 grams of t-butanol was placed in the stillpot of the same column used in example 4 and heat applied. When refluxing began, an extractive agent comprising 80% methyl benzoate, 20% salicylic acid was fed to the top of the column at a feed rate of 20 ml/min. and a temperature of 70°–75° C. After establishing the feed rate of the extractive agent, the heat input to the ethanol - t-butanol in the stillpot was adjusted to give a total reflux rate of 10–20 ml/min. Having established the reflux rate, the column was allowed to operation for one hour. After one hour of steady operation, overhead and bottoms samples of approximately two ml. were collected and analysed by gas chromatography. The overhead analysis was 85.4% ethanol, 14.6% t-butanol, the bottoms analysis was 63% ethanol, 37% t-butanol. Using these compositions in the Fenske equation with the number of theoretical plates in the column being 4.5, gave an average relative volatility of 1.32 for each theoretical plate. After 1.5 hours of total operation, the overhead composition was 86.8% ethaol, 13.2% t-butanol and the bottoms composition was 62.7% ethanol, 37.3% t-butanol. This gave and average relative volatility of 1.36 for each theoretical plate. After two hours of total operation, the overhead composition was 85.7% ethanol, 14.5% t-butanol and the bottoms composition was 63.2% ethanol, 36.8% t-butanol. This gave an average relative volatility of 1.34 for each theoretical plate.

What is claimed is:

1. A method for recovering ethanol from a mixture of ethanol and tertiary butanol which comprises distilling a mixture of ethanol and t-butanol in a rectification column in the presence of about one to two parts of extractive agent per part of ehtanol - t-butanol mixture, recovering ethanol as overhead product and obtaining the extractive agent and t-butanol from the stillpot, the extractive agent comprises at least a benzoate containing from seven to twenty-six carbon atoms.

2. The method of claim 1 in which the extractive agent comprises methyl benzoate.

3. The method of claim 1 in which the extractive agent comprises benzyl benzoate.

4. The method of claim 1 in which the extractive agent comprises ortho-hydroxy methyl benzoate (methyl salicylate).

5. A method for recovering ethanol from a mixture of ethanol and t-butanol which comprises distilling a mixture of ethanol and t-butanol in a rectification column in the presence of about one to two parts of extractive agent per part of ethanol t-butanol mixture, recovering ethanol as overhead product and obtaining the extractive agent and t-butanol from the stillpot, the extractive agent comprises a benzoate containing from seven to twenty-six carbon atoms and at least one material from the group consisting of benzoic acid, cinnamic acid, salicylic acid, phthalic anydride, hexahydrophthalic anhydride, methyl hexahydrophthalic anhydride, methyl tetrahydrophthalic anhydride and trimellitic anhydride.

6. The method of claim 5 in which the extractive agent comprises benzyl benzoate and at least one material from the group consisting of benzoic acid, salicylic acid, phthalic anhydride, hexahydrophthalic anhydride and methyl hexahydrophthalic anhydride.

7. The method of claim 5 in which the extractive agent comprises orth-hydroxy methyl benzoate (methyl salicylate) and at least one material from the group consisting of benzoic acid, cinnamic acid, salicylic acid, hexahydrophthalic anhydride, methyl hexahydrophthalic anhydride, trimellitic anhydride and dipropylene glycol dibenzoate.

8. A method for recovering ethanol from a mixture of ethanol and t-butanol which comprises distilling a mixture of ethanol and t-butanol in a rectification column in the presence of about one to two parts of extractive agent per part of ethanol- t-butanol mixture, recovering ethanol as overhead product and obtaining the extractive agent and t-butanol from the stillpot, the extractive agent comprises a hydrogenated phthalic anhydride containing from eight to nine carbon atoms.

9. The method of claim 8 in which the extractive agent comprises hexahydrophthalic anhydride and at least one material from the group consisting of benzoic acid, cinnamic acid, salicyclic acid, phthalic anhydride, methyl hexahydrophthalic anhydride and dipropylene glycol dibenzoate.

10. The method of claim 8 in which the extractive agent comprises methyl tetrahydrophthalic anhydride and at least one material from the group consisting of salicylic acid and dipropylene glycol dibenzoate.

11. The method of claim 8 in which the extractive agent comprises methyl hexahydrophthalic anhydride and at least one material from the group consisting of benzoic acid, salicylic acid, phthalic anhydride and dipropylene glycol dibenzoate.

* * * * *